United States Patent [19]

Tsuji et al.

[11] Patent Number: 4,971,700
[45] Date of Patent: Nov. 20, 1990

[54] METHOD OF CONTROLLING AMOUNT OF REMOVED WATER BY ULTRAFILTRATION AND CONTROL DEVICE FOR CONTROLLING AMOUNT OF REMOVED WATER BY ULTRAFILTRATION IN HEMODIALYSIS

[75] Inventors: Tsuyoshi Tsuji, Saitama; Masaaki Satoh, Tokyo; Yunoki Masayuki, Saitama, all of Japan

[73] Assignee: Med-Tech Inc., Tokyo, Japan

[21] Appl. No.: 180,952

[22] Filed: Apr. 13, 1988

[51] Int. Cl.$^5$ .................... B01D 61/26; B01D 61/28; B01D 61/34
[52] U.S. Cl. .................................. 210/647; 210/646; 210/650; 210/130; 210/137; 210/143; 210/188; 210/206; 210/257.2; 210/371.65; 210/321.71; 210/321.72; 210/929

[58] Field of Search ............ 210/90, 137, 188, 321.65, 210/321.71, 321.72, 929, 94, 143, 206, 257.2, 295, 646, 647, 650, 130

[56] References Cited

U.S. PATENT DOCUMENTS

| | | | |
|---|---|---|---|
| 4,037,616 | 7/1977 | Pinkerton | 210/321.71 |
| 4,209,391 | 6/1980 | Lipps et al. | 210/321.65 |
| 4,366,061 | 12/1982 | Papanek et al. | 210/321.65 |
| 4,477,342 | 10/1984 | Allan et al. | 210/321.71 |
| 4,676,905 | 6/1987 | Nagao et al. | 210/321.65 |

Primary Examiner—W. Gary Jones
Attorney, Agent, or Firm—Oblon, Spivak, McClelland, Maier & Neustadt

[57] ABSTRACT

The device for controlling the amount of removed water by ultrafiltration can eliminate the scaling error completely by the use of the diaphragms in the scaling mechanism, and thus, the water elimination precision can be improved.

3 Claims, 2 Drawing Sheets (a)    (b)    (c)

METHOD OF CONTROLLING AMOUNT OF REMOVED WATER BY ULTRAFILTRATION AND CONTROL DEVICE FOR CONTROLLING AMOUNT OF REMOVED WATER BY ULTRAFILTRATION IN HEMODIALYSIS

BACKGROUND OF THE INVENTION

It is an extremely important matter to control a precision of amount of removed water in a hemodialysis, and various methods have heretofore been employed such as adjusting a pressure at the blood side and a pressure at the dialysate side by means of a dialyzer through an ultrafiltration.

However, the elimination of water in the hemodialysis is such that an amount of removed water is an extremely small amount when compared with a flowrate of the dialysate so that in order to perform a water elimination control of a high precision, for example, there is a method of controlling the amount of removed water upon finding an ultrafiltration ratio intermittently. But, in general, since the ultrafiltration ratio is affected by a multitude of variable elements such as differences of physical properties according to kinds of dialyzers, differences of compositions of the bloods to be dialyzed or fluctuations with respect to the passage of time, it has been difficult to control the designated amount of removed water with a high precision. Also, in the clinic of the dialysis, as proteins, fats and the like are contained in the liquid discharge from the dialyzer, there are problems of causing errors in the measurement due to an adhesion to paths and scaling structure, and in a method of controlling an amount of removed water by using a piston pump and the like provided with mobile components, there are problems of increasing mobile resistance and accelerating wear and tear which result in errors due to the passage of time.

SUMMARY OF THE INVENTION

This invention has been conceived in view of the foregoing problems, and is to propose a novel method of controlling amount of removed water by ultrafiltration which is capable of controlling and correcting an amount of removed water in the hemodialysis, and its object is to provide a device for controlling amount of removed water by ultrafiltration which is capable of controlling the elimination of water with a high precision by working this method.

The method of controlling amount of removed water and the device for controlling amount of removed water in the hemodialysis according to this invention settle the problems with the basic concept described in the following. I. Basic concept in structure As shown in FIG. 1, the device for controlling amount of removed water in the hemodialysis of this invention is composed of the following as gists.

(1) Dialysate scaling chambers MCi, MCo which are independent are provided at a fluid supply side and a drainage side of a dialysate circuit.

(2) A suction pump PU is provided at a downstream of the scaling chamber MCo at the drainage.

(3) Electromagnetic valves Vi, VO, VB are provided which are capable of stopping a flow of the dialysate to a dialyzer DL and communicating a bypass circuit.

(4) The dialysate scaling chamber is provided with two pieces of right and left separate rooms which are sectioned by a diaphragm, and the two rooms are changed over to an inlet and outlet side alternately by changeover valves SVi and SVo at the inlet and the outlet of the chamber.

(5) Pressure detectors PSi, PSo are provided on a circuit at the side of a dialysate supply and a drainage side, and a central control unit CPU controlling the drive of the suction pump PU and the changeover valves SVi, SVo on the basis of its input information is provided. And more preferably, (6) Two pieces of diaphragms are provided in the dialysate scaling chamber of at least the fluid supply side or the drainage side of the dialyzer DL, and a volume of a central chamber between the diaphragms is subject to an increase and decrease.

II. Basic concept in controlling method

The method of controlling elimination of water by ultrafiltration is also composed of the following as gists.

(1) Changing over the changeover valves SVo, SVi of the outlet and inlet of the dialysate scaling chambers MCi, MCo which are independently provided at the fluid supply side and the drainage side of the dialyzer DL by a central control unit CPU on the basis of the pressure information from the pressure detectors PSo, PSi.

(2) Calculating differential values of signals obtained from the pressure detectors PSo, PSi by the central control unit CPU and operating the changeover valves SVo, SVi when the value come to be in the fixed range.

(3) Detecting a period of each changeover valve SVo, SVi of the fluid supply side and the drainage side and calculating the difference in the periods of the fluid supply side and the drainage side.

(4) Calculating an amount of removed water by the difference in the periods and controlling the suction pump PU so that it becomes equal to the required amount.

(5) It is difficult to make the volumes of the scaling chambers MCi, MCo at the fluid supply side and the drainage side equal strictly due to a precision limit of the materials and an adhesion of the wastes from the blood to the insides of the chambers. Accordingly, the electromagnetic valves VB for bypass is caused to open periodically (about two to three times per one dialysis), and the electromagnetic valves Vi, Vo are closed to stop the communication of the dialysate to the dialyzer DL, and in this condition, the changeover periods of the changeover valves SVi, SVo are detected, and the error due to the difference of the volumes of the scaling chambers is corrected by calculating the compensation value.

The correction of the error due to the difference in the volumes of the scaling chambers can be directly made without calculating the compensation value by providing a structure in which two pieces of the diaphragms are provided in either of the dialysate scaling chambers of the fluid supply side or the drainage side of the dialyzer DL, and the volume of the central chamber between the diaphragms is made subject to an increase and decrease.

(6) Namely, in the condition where the electromagnetic valve VB for bypass is made to open periodically, and the electromagnetic valves Vi, Vo are caused to close to stop the communication of the dialysate to the dialyzer DL, the volume control valve SVm provided on the scaling chamber MCo at the drainage side is caused to open. The changeover operation of the changeover valves SVi, SVo is caused to stop temporarily for both the fluid supply side and the drainage side, and all the dialysate in the chamber at the side of supplying the fluid to the dialyzer DL of the scaling chamber MCi at the fluid supply side is fed to the dialyzer DL and after a while, the volume adjusting valve SVm is caused to close.

Thereafter, the changeover operation is caused to start again to release the bypass condition.

The difference in the volumes of the scaling chamber MCi at the fluid supply side and the scaling chamber MCo at the drainage side is corrected by the fluid flowing into the diaphragm of the scaling chambers MCo at the drainage side.

DETAILED DESCRIPTION OF THE INVENTION

Figure 1:
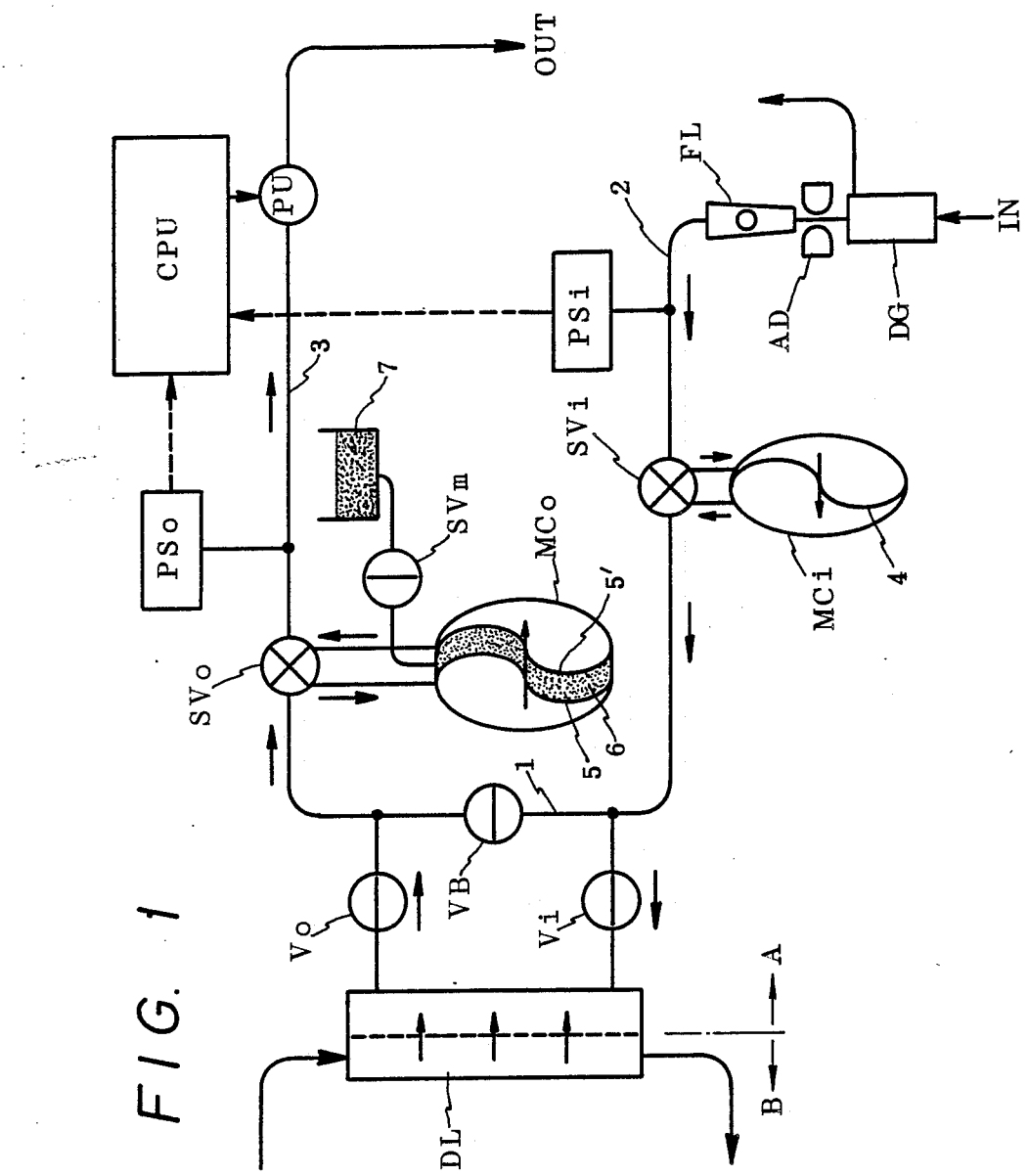
FIG. 1 is a circuit diagram of the dialysate of the device for controlling amount of removed water by ultrafiltration according to this invention.

The foregoing controlling method will be described in detail in the following.

The volume of the dialysate scaling chamber MCo at the drainage side is designated Vo, and the volume of the dialysate scaling chamber at the fluid supply side is made as Vi, and the dialysate flowrate is designated A, and in the bypass condition, the period of the changeover valve SVi at the fluid supply side is made as Ti, and the period of the changeover valve SVo at the drainage side is designated To, $$Ti = Vi/A \tag{1}$$

$$To = Vo/A$$

accordingly, $$Vo = (To/Ti)*Vi$$

Therefore, the compensation coefficient is made as $\beta$, $$\beta = To/Ti \tag{2}$$

In the dialysis, the period of the changeover valve SVi at the fluid supply side is made as Ti, and the period of the changeover valve SVo at the drainage side is made as To, and the difference in the periods is made as T, the relationship with the speed of removed water $\alpha$ is $$\begin{aligned} T &= Ti - To \\ &= (Vi/A) - (\beta*Vi/A + \alpha) \\ &= \{(1-\beta)*A + \alpha)\}/\{A*(A + \alpha)*Vi\} \end{aligned} \tag{3}$$

$A = Vi/Ti$ according to the formula (1), so that A is eliminated from the formula (3) and $\alpha$ is calculated by $$\alpha = [Vi*\{(1-\beta) - T/Ti\}]/(T-Ti)$$

so that the speed of removed water $\alpha$ can be obtained by measuring T and Ti.

The amount of removed water can be obtained as the product of speed of removed water and time.

Also, provided that the construction is arranged to make the volume of the central chamber between the diaphragms adjustable and the volumes of the scaling chamber MCo at the drainage side and the volume of the scaling chamber MCo at the drainage side are coincided directly, $Vi = Vo$ $\beta = 1$ so that the formula (3) becomes as follows:

$$\alpha = Vi*(-T/Ti)/(T-Ti) \tag{4}$$

Accordingly, the feasibility of adjustment of making the volumes of the scaling chamber at the drainage side and the scaling chamber at the fluid supply side to be equal means that errors caused by the change of volume of the scaling unit due to the expansion by temperature or the mechanical abrasion can be always corrected, and thus, the precision function can be guaranteed.

Also, as the scaling mechanism is constructed by the diaphragms, the scaling error occurring in the operation can be eliminated completely, and the precision of water elimination can be improved, and the high precision water elimination control by ultrafiltration in the hemodialysis can be achieved by the construction without the wear and tear of the scaling circuit and the generation of bubbles.

Embodiments

The method of controlling the amount of removed water by ultrafiltration and the device for controlling the amount of removed water in the hemodialysis of this invention will be described in the following by referring to the drawings.

FIG. 1 shows a dialysate circuit of the device for controlling amount of removed water by ultrafiltration according to this invention, and the A side of the dialyzer DL is the dialysate side, and the B side is the blood side. Symbols Vi and Vo denote the electromagnetic valve at the inflow side and the electromagnetic valve at the outflow side provided on the dialysate supply side and the flow path at the drain side of the dialyzer DL respectively, and thus, the bypass flow path 1 having the electromagnetic valve VB for bypass is formed, and the electromagnetic valve Vi at the inflow side is connected to the deaerating device DG provided in IN at the fresh dialysate supply side by means of the changeover valve SVi to form a circuit 2 at the dialysate supply side. Also, the electromagnetic valve Vo at the drain side is connected to the suction pump PU in the upperstream of DRAIN at the waste dialysate drain side by means of the changeover valve SVo to form a waste fluid circuit 3, and both the changeover valves SVi, SVo are controlled by the input information from the pressure detectors PSi, PSo provided on the circuit 2 at the dialysate supply side and the waste fluid circuit 3, and moreover, they are driven by the central control unit CPU that controls the suction pump PU by detecting the changeover times. The symbol MCi denotes the scaling chamber at the fluid supply side which is branch connected to the changeover valve SVi, and is sectioned by the diaphragm 4, and is provided with two pieces of right and left separated rooms (refer to FIG. 2) whose outlet and inlet sides are reversed by the changeover valve SVi, and the diaphragm 4 spreads along the right and left of the inner wall opposed by a lubricating film such as silicone rubber thin film and the like which does not paste nor contact the inner wall of the chamber. Also, the symbol MCo denotes the scaling chamber at the drainage side which is branch connected to the changeover valve SVo, and is provided with two pieces of left and right separated rooms sectioned by two sheets of diaphragms 5, 5' which reverse the outlet and inlet sides by the changeover valve SVo and the central chamber 6 between the diaphragms 5, 5', and the diaphragms 5, 5' are formed of a lubricating film such as the silicone rubber thin film and the like which does not paste nor contact the inner wall of the chamber similar to the scaling chamber SVi at the fluid supply side, and spread in the right and left of the opposed inner walls. In the scaling chamber MCo at the drainage side, the central chamber 6 communicates with a fluid reservoir 7 by means of the volume adjusting valve SVm. Also, on the part of the circuit 2 at the dialysate supply side to be supplied from the deaerating device DG, a bubble detector AD and a float FL are formed.

Figure 2:
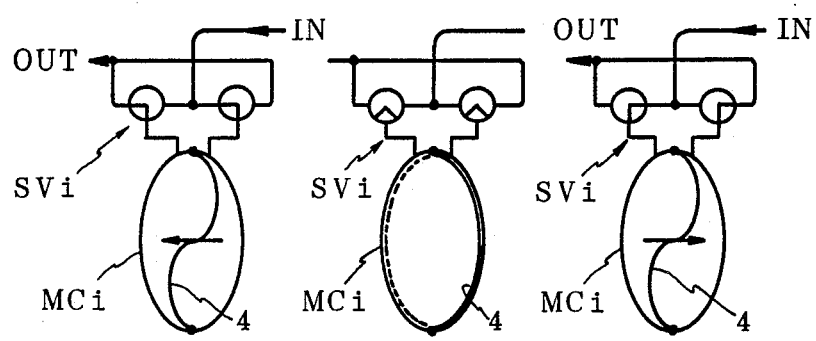
FIG. 2 is an operation explanatory drawing of the scaling chamber at the fluid supply side, wherein (a) denotes a condition in which the fluid flows into a right room and the fluid outflows from the left room, (b) denotes a condition in which the changeover valve is in operation condition, and (c) denotes a condition in which the fluid flows into the left room and the fluid outflows from the right room.
Figure 3:
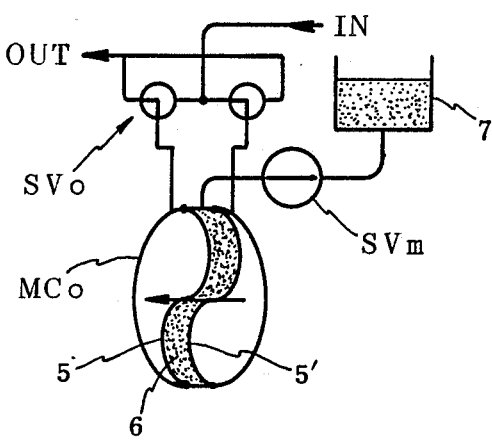
FIG. 3 is an operation explanatory drawing showing that the fluid flows into the right room of the scaling chamber at the drainage side and the fluid outflows from the left room.

The device for controlling amount of removed water having the foregoing construction is to flow the deaerated and fresh dialysate to the one side room of the scaling chamber MCi at the fluid supply side by means of path of the changeover valve SVi by the degassing device DG, and the diaphragm 4 that partitions the room is expanded and shifted to fill at its full capacity (refer to FIG. 2).

The diaphragm 4 is of construction of spreading in the right and left of the opposed inner walls and when the incoming dialysate fills the one side room of the scaling chamber MCi at the fluid supply side and the flow stops at that moment, the pressure of the pipeline at the inflow side sharply rises. The pressure rising phenomenon can be detected by the pressure detector PSi, and the changeover valve SVi can be operated by the signal. When the changeover valve SVi is operated, the dialysate flows into the room of the opposite side of the scaling chamber MCi at the fluid supply side, and the pressure of the circuit 2 at the dialysate supply side which is detected by the pressure detector PSi returns to the original pressure. The operation ranging from the detection of the fill of the one side room to the change of the inflow path is an instant operation, and the fluid paths of both the separated rooms can be simultaneously changed by the changeover valve SVi, and the one side room to which the fluid flowed in before the changeover sends the fresh dialysate to the circuit of the dialyzer DL by the changeover of the path. Also, the waste fluid passing through the dialyzer DL is led to the scaling chamber MCo at the drainage side of a volume equal to that of the scaling chamber MCi at the fluid supply side, and the operation is taken place with the inflow of the waste fluid and the drain thereof alternately to the left and right rooms, and the fluid is sucked positively by the suction pump PU.

In the central chamber 6 of the scaling chamber MCo at the drainage side, the liquid of non-volatile type (silicone oil, paraffin oil and the like) without the bubble or solvent gas is filled at its full capacity, and the communication between the fluid reservoir 7 and the central chamber 6 is closed by closing the volume adjusting valve SVm, and the volume in the central chamber 6 is made adjustable to control the volume of the scaling chamber MCo at the drainage side. The pressure signals of inflow into the left and right rooms and filling are detected by the pressure detector PSo equipped between the scaling chamber MCo at the drainage side and the suction pump PU and the scaling is obtained by operating the changeover valve SVo.

The performance of constantly correcting the errors due to the change of volume by the expansion of the scaling unit by temperature or the mechanical wear and tear is an important element guaranteeing the precision performance.

The function of the hemodialysis is to eliminate the waste which is the uremic material from the blood, and its object is to provide the treatment of diffusion by the difference in the concentrations with the dialysate and perform an elimination of water, and the foregoing paragraph may be determined by the properties of the dialyzer, but the elimination of water content is physically performed by the pressure difference between the blood and the dialysate by means of the film of the dialyzer. In view of physiology, the amount of water content in the human body is an important element for life, and the proper control is required on the dialysis machine. Also, in recent years, the film manufacturing technique of the dialyzer is improved, and an improvement of the water elimination performance is remarkable and the execution of the planned water elimination control and the precision and maintenance and control of the dialysis machine are becoming important.

At present, even in the dialysis machines being currently used in the clinics, there are problems such as the use of piston pumps or link mechanism producing the errors due to the wear and tear on the central functional components which measure and eliminate water and in addition, the use of a structure of generating the bubbles such as gear pumps in the fluid circuit between the scaling units, and therefore, safety and stability are important in carrying out the control of water elimination.

However, in this invention, with the adjustment of the volumes of the scaling chamber MCi at the fluid supply side and of the scaling chamber MCo at the waste fluid side to be equal at the start time of the dialysis, the errors due to the change of volume by the expansion of the scaling unit by temperature or the mechanical wear and tear can be constantly corrected, which is an important element for guaranteeing the precision function, and by this element, the device can maintain the high precision for many years, and particularly, the error at the time of designation of the low amount of water elimination can be held down.

As described in the foregoing, the device for controlling the amount of removed water by ultrafiltration according to this invention can eliminate the scaling error completely by the use of the diaphragms in the scaling mechanism, and thus, the water elimination precision can be improved, and the effect of this invention upon its working is extremely great.

What is claimed is:

1. A device for controlling the amount of removed water in a hemodialysis, comprising:

a dialyzer;

a plurality of electromagnetic valves for controlling flow of dialysate to said dialyzer;

means defining a first dialysate scaling chamber having a right and left partition separated by a diaphragm on a fluid supply side of said dialyzer;

means defining a second dialysate scaling chamber including a right and left partition provided independently and sectioned by second diaphragm wherein said second scaling chamber is provided on a drainage side of said dialyzer;

first and second changeover valves respectively provided in association with said first and second scaling chambers wherein said right and left sectioned partitions of each of said chambers are changed alternately between an inlet side and an outlet side of said first and second changeover valves provided at each inlet and outlet;

a suction pump provided down stream of said second scaling chamber;

a bypass circuit provided by said plurality of electromagnetic valves to stop communication of dialysate to said dialyzer when said bypass circuit is formed;

a first and second pressure detector means provided at the dialysate supply side and drainage side respectively of the dialyzer; and a central control unit for controlling drive of said suction pump and both of said changeover valve on the basis of input information received from said pressure detectors wherein said diaphragm on at lest one of said first and second dialysate scaling chamber includes two portions to form a central chamber between said two portions of said diaphragm and wherein said central chamber is adjustable and includes a means for introducing fluid into said central chamber.

2. The device according to claim 1 further including a deaerating device having a bubble detector which is provided in a circuit upstream of said first pressure detector at the dialysate supply side.

3. A method of correcting an amount of removed water in a hemodialysis which comprises:

a dialyzer;

a plurality of electromagnetic valves for controlling flow of the dialysate to said dialyzer;

means defining a first dialysate scaling chamber having a right and left partition separated by a diaphragm on a fluid supply side of said dialyzer;

means defining a second dialysate scaling chamber including a right and left partition provided independently and sectioned by a second diaphragm wherein said second scaling chamber is provided on a drainage side of said dialyzer;

first and second changeover valves respectively provided in association with said first and second scaling chamber wherein said right and left sectioned partitions of each of said chambers are changed alternately between an inlet side and an outlet side by said first and second changeover valves provided at each inlet and outlet;

a suction pump provided downstream of said second scaling chamber;

a bypass circuit provided by said plurality of electromagnetic valves to stop communication of dialysate to said dialyzer when said bypass circuit is formed;

a first and second pressure detector means provided at the dialysate supply side and the drainage side respectively of the dialyzer; and a central control unit for controlling drive of said suction pump and both of said changeover valves on the basis of input information received from said pressure detectors, comprising the steps of;

providing a volume adjusting valve in conjunction with said second scaling chamber;

opening said volume adjusting valve when said one of said electromagnetic valves for said bypass is open and when said others of said electromagnetic valves are closed to stop communication of said dialysate to said dialyzer;

stopping the changeover operation of said changeover valves;

feeding said dialysate in said partition at the side of supplying fluid to said dialyzer of said first scaling chamber;

closing said volumes adjusting valve after a predetermined time;

releasing the bypass condition by starting said changover operation; and correcting a volume difference of said first scaling chamber and said second scaling chamber by means of fluid flowing into a central partition of said second scaling chamber.

* * * * *

UNITED STATES PATENT AND TRADEMARK OFFICE
CERTIFICATE OF CORRECTION

PATENT NO. : 4,971,700
DATED : November 20, 1990
INVENTOR(S) : Tsuyoshi Tsuji et al.

It is certified that error appears in the above-identified patent and that said Letters Patent is hereby corrected as shown below:

On the title page, item [75] Inventors:

"Yunoki Masayuki", should be, --Masayuki Yunoki--.

Signed and Sealed this

Eighth Day of September, 1992

*Attest:*

DOUGLAS B. COMER

*Attesting Officer*     *Acting Commissioner of Patents and Trademarks*